United States Patent [19]
Doudican et al.

[11] Patent Number: 5,798,463
[45] Date of Patent: Aug. 25, 1998

[54] SELF-CONTAINED CONSTANT STRESS/CONSTANT STRAIN TEST FIXTURE

[75] Inventors: John C. Doudican, Tulsa, Okla.; Edward M. Hagerman, Royal Oak, Mich.; John M. Henshaw, Tulsa, Okla.; Laura J. Meyer, Urbana, Ill.; Daniel Q. Houston, Dearborn, Mich.

[73] Assignees: Automotive Composites Consortium, Mich.; University of Tulsa, Okla.

[21] Appl. No.: 797,971

[22] Filed: Feb. 12, 1997

[51] Int. Cl.[6] ................................................ G01D 1/16
[52] U.S. Cl. .................................. 73/789; 73/796; 73/856
[58] Field of Search ............................... 73/760, 789, 794, 73/790, 796, 818, 826, 828, 831, 833, 856, 860

[56] References Cited

U.S. PATENT DOCUMENTS

| | | |
|---|---|---|
| 1,819,232 | 8/1931 | Cropper . |
| 3,005,336 | 10/1961 | Wyman . |
| 3,139,684 | 7/1964 | Boyle ............................ 73/826 |
| 3,319,338 | 5/1967 | De Nicola ........................ 73/820 |
| 3,331,242 | 7/1967 | Schwarz et al. . |
| 3,826,902 | 7/1974 | Claxton et al. ................... 73/789 |
| 3,916,681 | 11/1975 | Ryckman et al. ................. 73/857 |
| 4,232,446 | 11/1980 | Woods et al. . |
| 4,594,900 | 6/1986 | Pellerin et al. .................. 73/837 |
| 5,388,464 | 2/1995 | Maddison ........................ 73/856 |
| 5,394,754 | 3/1995 | Herring, Jr. . |
| 5,505,095 | 4/1996 | Raymond ........................ 73/851 |

*Primary Examiner*—Richard Chilcot
*Assistant Examiner*—Max H. Noori
*Attorney, Agent, or Firm*—Reising, Ethington, Barnard & Perry

[57] ABSTRACT

A tensile test fixture for applying constant tensile forces to a tensile test specimen comprises two mounting grips, each mounted to one of two lever arms in a pivoted lever arm frame structure. One end of each lever arm is pivotally attached to a compression column while the other end of each lever arm is attached to one end of a force-applying assembly. The mounting grips are pivotally attached to their respective lever arms between the compression column and the force-applying assembly and are designed to hold opposite ends of a tensile test specimen. The force-applying assembly comprises stress and strain modules that are interchangeably installable into the force-applying assembly to selectively subject tensile test specimens to constant strain and constant stress.

16 Claims, 2 Drawing Sheets

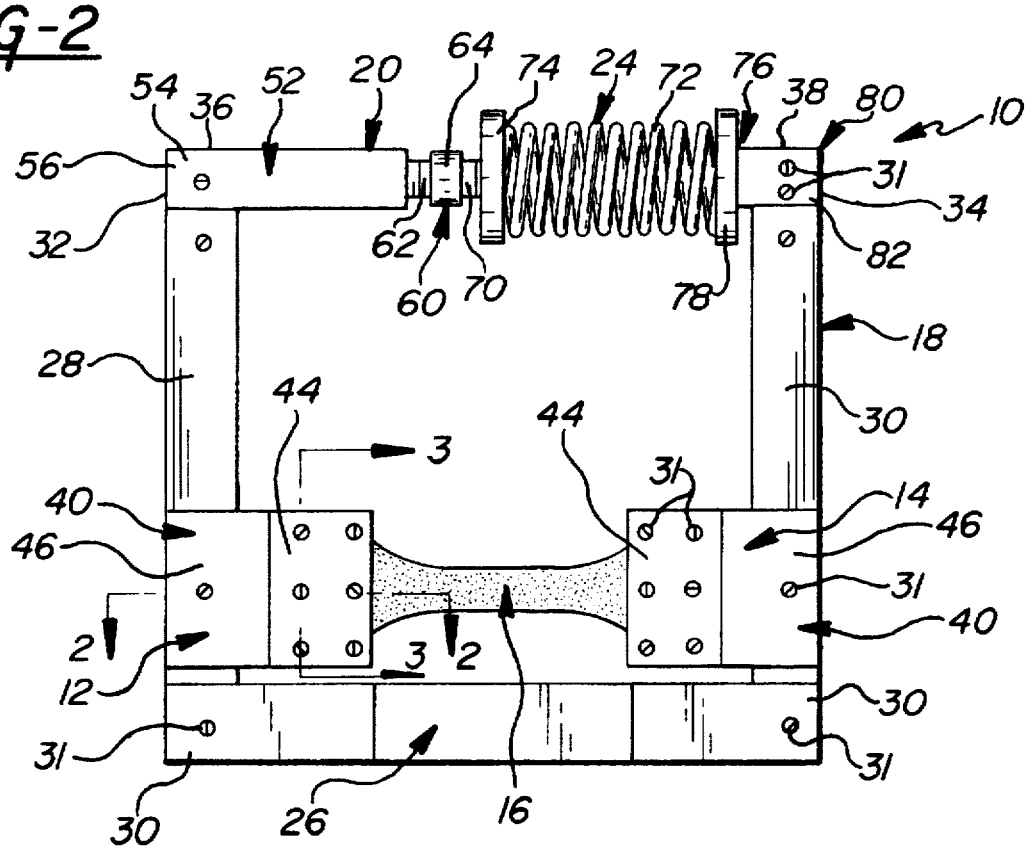
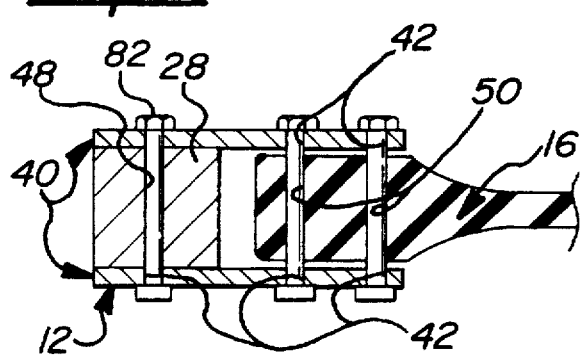
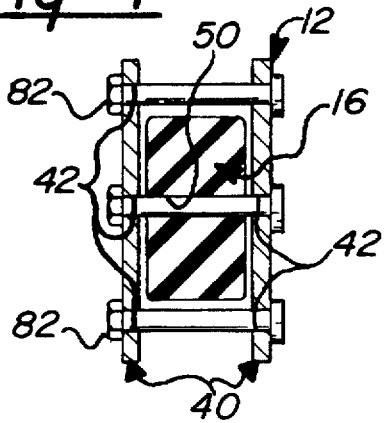

SELF-CONTAINED CONSTANT STRESS/ CONSTANT STRAIN TEST FIXTURE

TECHNICAL FIELD

This invention relates generally to a tensile test fixture and, more particularly, to such a test fixture that is small enough to be used in a confined space.

BACKGROUND OF THE INVENTION

Mechanical stress and strain can accelerate deleterious environmental effects on the durability of certain construction materials, e.g., materials used to fabricate automotive components. Therefore, to ensure the durability of such materials, it is important to test those materials by subjecting them to mechanical stress and strain under the environmental conditions they will be subjected to. In other words, to better predict the long-term behavior of such materials, it is often advisable to observe their resistance to a combination of mechanical loading and a harsh environment. This type of stressed environmental testing has been done in the laboratory using mechanical testing machines fitted with environmental chambers, but such devices are large and expensive. In addition, it is seldom practical to use such devices in the field.

As a result, smaller test fixtures have been developed for use either in the laboratory or in the field. For example, U.S. Pat. No. 5,388,464 to Maddison discloses a tube-shaped test fixture that subjects a tensile test specimen to varying stresses. The fixture is sufficiently small to be used in confined spaces, such as the underside of a vehicle or within a vehicle engine compartment. However, the Maddison test fixture does not subject test specimens to constant strain.

Another example of a small test fixture is disclosed in U.S. Pat. No. 3,331,242 issued to Schwarz et al. Schwarz et al. disclose a test fixture with a rectangular box-shaped frame comprising upper and lower specimen holders connected by a pair of threaded guide rods. The test fixture is designed to simultaneously subject a number of test specimens to constant strain. However the Schwarz et al. fixture does not subject test specimens to constant stress.

What is needed is a single compact, self-contained device capable of subjecting a test specimen to both constant stress and constant strain while exposing the specimen to any of a number of test environments, either in the laboratory or in the field.

SUMMARY OF THE INVENTION

In accordance with this invention a tensile test fixture is provided with interchangeable stress and strain modules that allow constant stress and constant strain testing to be carried out using a single test fixture. The test fixture comprises first and second mounting grips for holding opposite ends of a tensile test specimen and a frame that supports the first and second mounting grips for relative reciprocal movement toward and away from one another. The test fixture also comprises a force-applying assembly that includes a strain module that is connectable between the first and second mounting grips to subject tensile test specimens to constant strain. The force applying module also includes a stress module that is connectable between the first and second mounting grips to subject tensile test specimens to constant stress.

According to one aspect of the present invention the stress and strain modules are constructed to be interchangeably insertable into the force-applying assembly. Test personnel can easily interchange the two modules as necessary to adapt the fixture to subject a tensile test specimen to either constant stress or constant strain.

According to another aspect of the present invention the frame comprises a pivoted lever arm frame structure. The pivoted lever arm frame structure comprises a pair of lever arms that are pivotally connected to a compression column and extend transversely to lever arm force-application points where they connect to opposite ends of the force-applying assembly. The first and second mounting grips are connected to the lever arms between the compression column and the force-applying assembly. This levered arrangement provides mechanical advantage that increases the amount of tensile force applied to a test specimen for a given amount of outward force exerted at the force-application points of the lever arms.

According to another aspect of the present invention, at least one of the lever arm force-application points comprises a pivotal connection to the force-applying assembly.

According to another aspect of the present invention, at least one of the lever arm force-application points comprises a releasable connection to the force-applying assembly. This allows test personnel to easily disconnect an end of the force-applying assembly that comprises the stress or strain module to aid in interchanging the modules.

According to another aspect of the present invention, the force-applying assembly comprises a first bolt holder that is pivotally attached to the first lever arm. The first bolt holder also includes a threaded bore for receiving a first threaded end of a load bolt in threaded engagement.

According to another aspect of the present invention, the strain module comprises a second bolt holder that pivotally connects to the second lever arm and includes a threaded bore for receiving a second threaded end of the load bolt in threaded engagement. The second threaded end of the load bolt and the threaded bore of the second bolt holder are threaded in an opposite helical direction from the first threaded end and from the threaded bore of the first bolt holder. The opposite threading forces the lever arms apart when the load bolt is turned in one direction and draws the lever arms together when the load bolt is turned in the other direction.

According to another aspect of the present invention, the stress module comprises a spring retained by inner and outer spring retainers. The inner retainer includes a threaded aperture for receiving the second threaded end of the load bolt in threaded engagement. The outer spring retainer includes a releasable lever arm connector for releasably connecting to one of the lever arms.

According to another aspect of the present invention, the lever arm connector of the outer spring retainer is a fixed non-pivotal connector. This connection is prevented from pivoting to prevent the spring from buckling under side loads.

According to yet another aspect of the present invention, a method is provided for selectively subjecting tensile test specimens to constant stress and constant strain by constructing the test fixture described above, installing either the stress module or the strain module, attaching a tensile test specimen to the mounting grips, adjusting the force-applying assembly to apply a desired amount of stress or strain, as applicable, placing the specimen and tensile test fixture in a desired test environment for a desired test period, interchanging the modules, and again adjusting the force-applying assembly to apply the desired amount of stress or strain, as applicable. The test specimen may be replaced when the modules are interchanged.

BRIEF DESCRIPTION OF THE DRAWINGS

To better understand and appreciate the invention, refer to the following detailed description in connection with the accompanying drawings:

FIG. 2 is a top view of the test fixture of FIG. 1;

FIG. 3 is a cross-sectional view of the test fixture of FIG. 2 taken along line 3—3 of FIG. 2;

FIG. 4 is a cross-sectional view of the test fixture of FIG. 2 taken along line 4—4 of FIG. 2.

DETAILED DESCRIPTION OF THE PREFERRED EMBODIMENT

Figure 5:
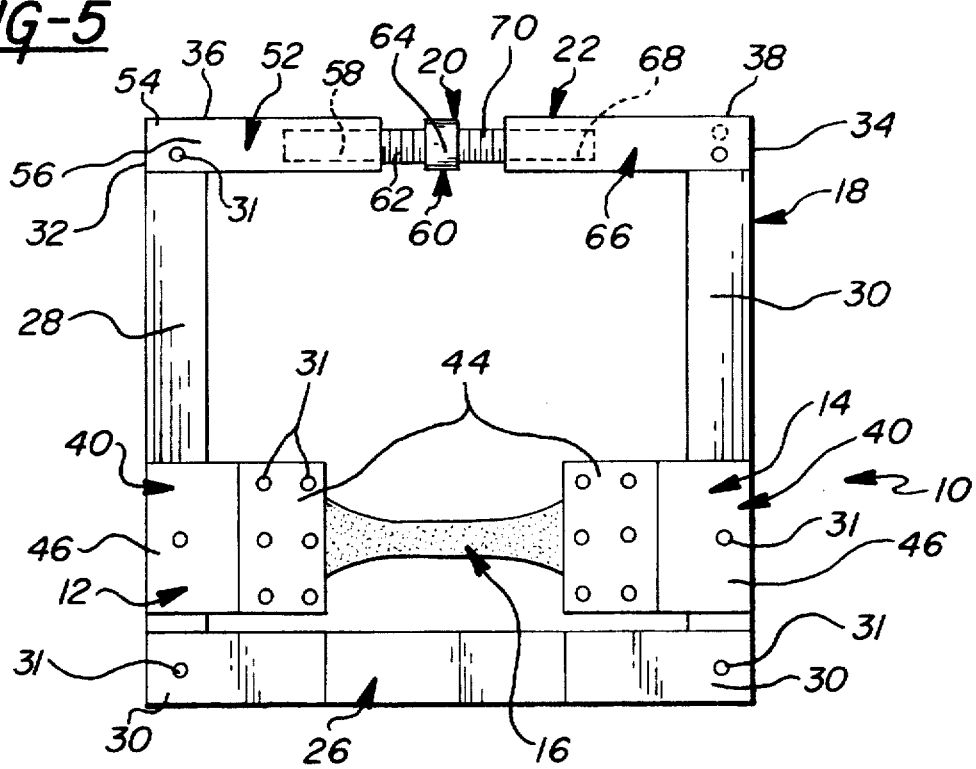
FIG. 5 is a top view of a test fixture constructed according to the present invention and including a strain module for applying constant strain to a tensile test specimen.
Figure 1:
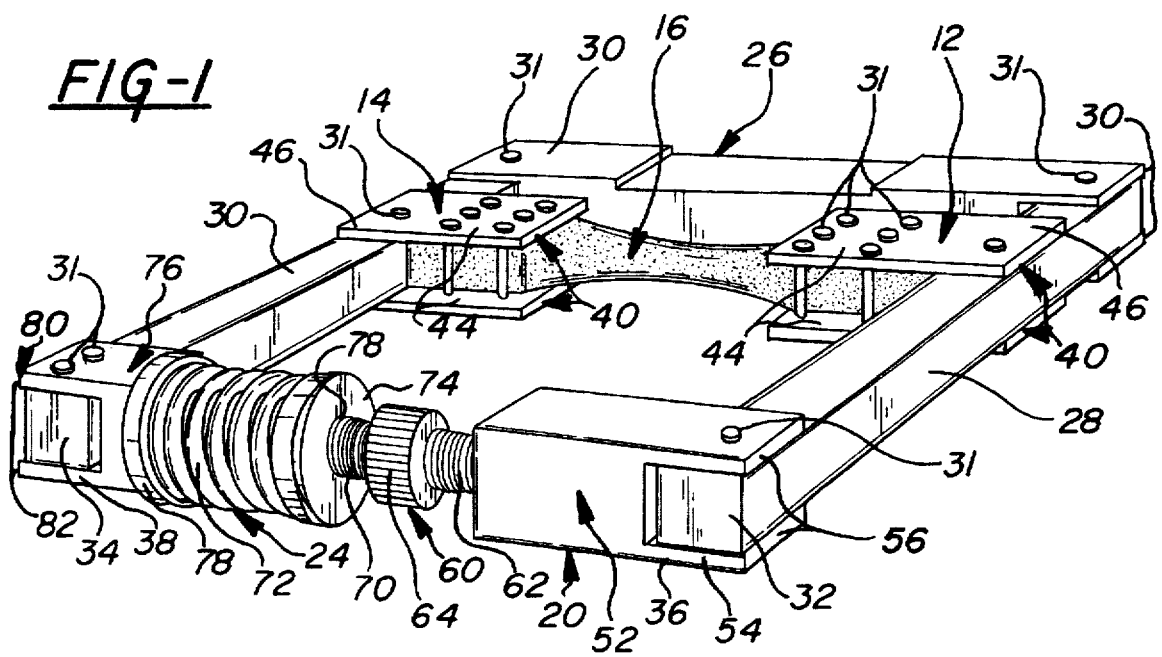
FIG. 1 is a perspective view of a tensile test fixture constructed according to the present invention and including a stress module for applying constant stress to a tensile test specimen.

A composite tensile test fixture constructed according to the present invention is shown at 10 in FIGS. 1, 2 and 5. The test fixture 10 comprises first 12 and second 14 mounting grips for holding opposite ends of a tensile test specimen 16 and a frame 18 that supports the first 12 and second 14 mounting grips. A force-applying assembly 20 is connected between the first 12 and second 14 mounting grips, but need not be connected directly to the mounting grips 12, 14. The force-applying assembly 20 includes one of two interchangeable modules: a strain module as shown at 22 in FIG. 5 or a stress module as shown at 24 in FIGS. 1 and 2. The strain module 22 adapts the force-applying assembly 20 to subject the specimen 16 to constant strain while the stress module 24 adapts the force-applying assembly 20 to subject the specimen 16 to constant stress.

In other embodiments, the stress module 24 and the strain module 22 may each make-up an entire force-applying assembly rather than a component of the force-applying assembly 20. In such embodiments, the entire force-applying assembly becomes interchangeable rather than a portion of the force-applying assembly 20. The test fixture 10 may, therefore, include releasable connections that allow test personnel to interchange entire force-applying assemblies that are dedicated solely to subjecting a specimen 16 to either constant stress or constant strain.

The frame of the present embodiment, shown at 18 in FIGS. 1, 2 and 5, comprises a pivoted lever arm frame structure that includes a compression column 26 pivotally connected to first 28 and second 30 lever arms. The compression column 26 comprises an elongated stainless steel bar having a square or rectangular cross section. Located adjacent each opposite end of the compression column 26 are connecting points. At each connecting point two parallel flat, rectangular prongs 30 extend longitudinally outward from each end of the compression column 26. Each prong 30 includes a circular through-bore for receiving a connecting pivot pin 31.

The lever arms 28, 30 are elongated stainless steel bars with square or rectangular cross-sections. The first 28 and second 30 lever arms extend transversely from their respective first and second compression column connecting points to respective first 32 and second 34 force-application points located at the distal ends of the lever arms 28, 30. The first 28 and second 30 lever arms are connected at their respective first 32 and second 34 force-application points to opposite ends 36, 38 of the force-applying assembly 20, respectively.

At each compression column connecting point, the lever arms 28, 30 are disposed between the parallel prongs 30 that extend from each end of the compression column 26. Each compression column connecting point of each lever arm 28, 30 also includes a circular through bore that lies in axial alignment with the two flanking through-bores located in the compression column connecting prongs 30.

Also at each compression column connecting point a flat-headed connecting pivot pin 31 passes through both prong through-bores and the coaxially-disposed lever arm through-bore. Each pin 31 includes a threaded shaft at one end with a nut threadedly engaged on the threaded shaft to hold each pin in a fixed position in relation to the prongs.

The first 12 and second 14 mounting grips are pivotally supported on the first 28 and second 30 lever arms, respectively. The first mounting grip 12 is disposed between the first compression column connecting point and the first 32 force-application point. The second mounting grip 14 is disposed between the second compression column connecting point and the second 34 force-application point.

Each mounting grip 12, 14 comprises a pair of parallel, spaced-apart rectangular stainless steel plates 40. As shown in FIGS. 3 and 4, each mounting grip plate 40 includes an identical pattern of seven holes 42 for receiving mounting pins 31. Six of the holes 42 are arranged on an inner half 44 of each plate 40 in two transversely-oriented parallel rows of three as is best shown in FIGS. 2 and 5. The remaining hole is disposed through an outer half 46 of each plate. The outer half of the plates 40 of the first mounting grip 12 are disposed flush against opposite surfaces of the first lever arm 28. Likewise, the outer half of the plates 40 of the second mounting grip 14 are disposed flush against opposite surfaces of the second lever arm 30. A through-hole, shown at 48 in FIG. 3, passes through each lever arm 28, 30 and is coaxially aligned with the holes 42 disposed in the outer halves 46 of the plates 40. A threaded connecting pivot pin 31 passes through each set of coaxially aligned holes 42, 48 to pivotally fasten each set of plates 40 to their respective lever arm 28, 30.

For each mounting grip 12, 14, the center two of the holes 42 in the inner end 44 of each plate 40 are axially aligned with each other. Threaded pins extend through each of these sets of coaxially-aligned holes and through holes 50 in the test specimen 16 to hold test specimen 16 in place. Nuts, shown at 82 in FIGS. 3 and 4, threadedly engage threaded ends of each pin 31 to hold the pins 31 in place. As shown in FIG. 4, threaded pins 31 also extend through the remaining four sets of the holes 42 in each pair of mounting grip plates 40 and are fastened in place by nuts 82 at their threaded ends.

In a test fixture 10 configured to apply constant strain as shown in FIG. 5, the first 32 and second 34 lever arm force-application points each comprise a pivotal connection to the force-applying assembly 20. However, when the fixture 10 is configured to subject a test specimen 16 to constant-stress as shown in FIGS. 1 and 2, a pivotal connection is included at only one of the lever arm force-application points 32, 34.

As shown in FIGS. 1, 2 and 5 the force-applying assembly 20 comprises a first bolt holder 52 having an elongated stainless steel bar with a square or rectangular cross-section and an outer end 54 pivotally connected to the first lever arm 28. The first bolt holder 52 includes a pair of flat rectangular prongs 56 that extend longitudinally from the first bolt holder outer end 54 in a parallel relationship to one another. The distance between the parallel prongs 56 is slightly greater than the thickness of the first lever arm 28 so that the first lever arm 28 can be inserted between the prongs 56. Each prong 56 includes a through hole that axially aligns with a corresponding hole extending through the first lever arm 28 adjacent the first force-application point 32. The first bolt holder 52 is connected to the first lever arm 28 by a pivot pin 31 that extends through the holes in the prongs and the corresponding hole in the first lever arm 28. The pivot pin 31 at this connection is fastened in place in the same manner as the pivot pins 31 described above.

A threaded bore, shown hidden at 58 in FIG. 5, extends into the first bolt holder bar from an inner end of the bar opposite the outer end 54. The force-applying assembly 20 also includes a load bolt, shown at 60 in FIGS. 1, 2 and 5, having a first threaded end 62 that is threadedly and adjustably engaged within the threaded bore 58 of the first bolt holder 52. Adjacent the first threaded end 62, the load bolt 60 includes a radially-extending circumferential adjustment flange 64. The adjustment flange 64 provides a serrated gripping surface for an operator to grasp and adjust the position of the load bolt 60 within the first bolt holder 52.

The strain module, shown at 22 in FIG. 5, comprises a second bolt holder 66 that is pivotally and releasably connectable to the second lever arm 30. The second bolt holder 66 is identical to the first bolt holder 52 except that its threaded bore, shown hidden at 68, is adapted to receive and threadedly engage a second threaded end 70 of the load bolt 60. The second threaded end 70 of the load bolt 60 is identical to the first threaded end 62 of the load bolt 60 except that the threads of the second threaded end 70 are cut in a direction helically opposite to those of the first threaded end 62. Consequently, the threaded bore 68 of the second bolt holder 66 is threaded in an opposite helical direction from the threaded bore 58 of the first bolt holder 52. Because the threads are helically opposite, when the strain module 22 is installed in the force-applying assembly 20, a turn of the bolt 60 in one direction will force the two bolt holders 52, 66 apart while a turn in the opposite direction will draw the two bolt holders 52, 66 together.

As shown in FIGS. 1 and 2, the stress module 24 comprises a coil or "helical" spring 72 retained by inner 74 and outer 76 spring retainers. The inner spring retainer 74 comprises a stainless steel inner disk that abuts an inner end of the spring 72. The inner disk includes an aperture 78 that is coaxially aligned with the spring 72 and threaded to receive the second threaded end 70 of the load bolt 60 in threaded engagement.

The outer spring retainer 76 includes a stainless steel outer disk 78 that abuts an outer end of the spring 72 opposite the spring inner end, and includes a releasable lever arm connector 80. The lever arm connector 80 is fixed to the outer stainless steel disk 78 and is adapted to releasably and non-pivotally connect the stress module 24 to the second lever arm 30. More specifically, the lever arm connector 80 includes a pair of flat rectangular prongs 82 that extend axially of the outer stainless steel disk 78 in a parallel relationship to one another. The distance between the parallel prongs 82 is roughly equal to or slightly greater than the thickness of the second lever arm 30 so that the second lever arm 30 can be inserted between the prongs 82. Each of the prongs 82 includes two through holes that axially align with a corresponding pair of holes extending through the second lever arm 30 adjacent the second force-application point 34. The prongs 82 are connected to the second lever arm 30 by two pins 31 that extend through the holes in the prongs and the corresponding holes in the second lever arm 30. The pins 31 are fastened in place in the same manner as the pins 31 described above. The use of two rather than one pin 31 at this connection prevents pivoting which could promote spring buckling.

In other embodiments of the present invention the compression column 26 may be of any shape that allows it to support compressive loads exerted at the compression column connecting points. In the frame design, other types of pivotal connections may be used. The frame lever arms 28, 30 may be of any shape and composition that will support shear forces generated when force is applied at the force application points 32, 34 and transmitted to the mounting grips 12, 14. Many other mounting grip configurations are possible. The mounting grips may be of any shape or configuration that will hold test specimens 16 securely enough to prevent specimen slip. The mounting grip plates 40 may include other hole patterns and fasteners other than those of the present embodiment. Instead of a serrated gripping surface, the adjustment flange 64 may include other types of gripping surfaces such as hex bolt surfaces to provide engagement surfaces for a wrench or the like. Instead of a load bolt—bolt holder arrangement, the strain module 22 may comprise any suitable mechanical device capable of incrementally adjusting the distance between the lever arms 28, 30. Any of the above components may be fabricated from suitable materials other than stainless steel.

In practice, one or more tensile test specimens 16 may be selectively subjected to constant stress and constant strain by installing either the stress module 24 or the strain module 22 into a test fixture 10 constructed as described above, and attaching a tensile test specimen 16 to the test fixture mounting grips 12, 14.

The stress module 24 is installed by first screwing the second threaded end 70 of the load bolt 60 into the threaded aperture in the inner spring retainer 74 of the stress module 24. The outer spring retainer 76 of the stress module 24 is then fastened to the second lever arm 30 by aligning the four prong holes with the two corresponding holes in the second lever arm 30 and inserting two pins 31 through the two resulting sets of coaxially-aligned holes. Nuts, such as those shown at 82 in FIGS. 3 and 4, are then screwed onto the threaded ends of each of the two pins 31 to secure the pins in place.

The strain module 22 is installed by first screwing the second threaded end 70 of the load bolt 60 into the threaded bore of the second bolt holder 80 of the strain module 22. The holes in the strain module prongs are then axially aligned with the corresponding hole in the first lever arm 28. A pin 31 is then inserted through the coaxially-aligned holes and is fastened in place by screwing a nut onto its threaded end.

A tensile test specimen 16 is attached to the test fixture mounting grips 12, 14 by first drilling two holes 50 in each end of the specimen 16 as best shown in FIG. 4. The ends of the specimen 16 are then inserted between the spaced-apart rectangular stainless steel plates 40 of each mounting grip 12, 14. The two newly-drilled holes 50 in each end of the specimen 16 are then aligned with the center two holes on the inner end of each plate as shown in FIGS. 3 and 4. Threaded pins 31 are then inserted through each of these sets of coaxially-aligned holes 42, 50 to hold test specimens 16 in place. Nuts 82 are then screwed onto the threaded ends of the pins to hold the pins in place.

Once the stress or strain module 22 is installed and the specimen 16 attached, the force-applying assembly 20 is adjusted by turning the adjustment flange 64 on the load bolt 60. If the stress module 24 is installed, the load bolt 60 is turned until a desired level of stress is achieved. If the strain module 22 is installed, the load bolt 60 is turned until a desired amount of deflection, i.e., strain, is achieved in the test specimen 16.

Once the force-applying assembly 20 is adjusted, the specimen 16 and tensile test fixture 10 are placed in a desired test environment, such as the engine compartment of a car, for a desired test period. Alternatively, the specimen 16 and fixture 10 could be placed onto the underbody area of a vehicle where the specimen 16 would be exposed to the same environmental conditions it would be likely to see while operationally installed in such a vehicle.

The stress or strain module 22 (whichever was first installed) is then removed from the frame 18 by a straightforward reversal of the process described above. The other of the stress and strain module 22 is then attached to the frame 18 as described above. Once the other module 22, 24 is installed, the force-applying assembly 20 is adjusted as required.

After placing the test specimen 16 and test fixture 10 in a desired test environment the test specimen 16 may be detached from the mounting grips 12, 14 and replaced with a second test specimen rather than leaving the same specimen installed for both stress and strain testing.

A test fixture constructed according to the present invention saves time and money by allowing a single test fixture to support both stress and strain testing.

This is an illustrative description of the invention using words of description rather than of limitation. Obviously, many modifications and variations of this invention are possible in light of the above teachings. Within the scope of the claims one may practice the invention other than as described.

We claim:

1. A method for selectively subjecting tensile test specimens to constant stress and constant strain using a single test fixture comprising a frame supporting first and second mounting grips and a force-applying assembly comprising a strain module connectable between said first and second mounting grips to subject tensile test specimens to constant strain, said force-applying assembly additionally comprising a stress module interchangeably connectable between said first and second mounting grips in place of said strain module to subject tensile test specimens to constant stress, said method comprising the steps of:

constructing the test fixture;
installing one of the stress module and strain module;
attaching a tensile test specimen to the mounting grips;
adjusting the force-applying assembly;
placing the specimen and tensile test fixture in a desired test environment for a desired test period;
detaching the test specimen from the mounting grips;
removing the installed module;
installing the other of the modules to the frame;
attaching a second test specimen to the mounting grips ; and
adjusting the force-applying assembly.

2. A tensile test fixture for applying constant tensile forces to a tensile test specimen, said test fixture comprising:

first and second mounting grips for holding opposite ends of a tensile test specimen;
a frame supporting said first and second mounting grips for relative reciprocal movement toward and away from one another; and a force-applying assembly comprising a strain module connectable between said first and second mounting grips to subject tensile test specimens to constant strain;
said force-applying assembly additionally comprising a stress module connectable between said first and second mounting grips to subject tensile test specimens to constant stress; and
said stress module and said strain module are interchangeably connectable within said force-applying assembly.

3. A test fixture as defined in claim 2 said frame comprising a pivoted lever arm frame structure.

4. A test fixture as defined in claim 3 in which said force-applying assembly has first and second opposite ends and where said pivoted lever arm frame structure comprises:

a compression column pivotally connected to first and second lever arms;
said first and second lever arms extending transversely from respective first and second compression column connecting points to respective first and second force-application points;
said first and second mounting grips supported on said first and second lever arms, respectively, said first mounting grip disposed between said first compression connecting point and said first force-application point and said second mounting grip disposed between said second compression connecting point and said second force-application point, and
said first and second ends of said force-applying assembly connected to said first and second lever arm force-application points, respectively.

5. A test fixture as defined in claim 4 in which at least one of said lever arm force-application points comprises a pivotal connection to said force-applying assembly.

6. A test fixture as defined in claim 4 in which at least one of said lever arm force-application points comprises a releasable connection to said force-applying assembly.

7. A test fixture as defined in claim 4 in which said force-applying assembly comprises:

a first bolt holder including an outer end pivotally connected to said first lever arm, said first bolt holder including a threaded bore disposed in an inner end of said first bolt holder opposite said outer end; and
a load bolt having a first threaded end threadedly and adjustably engaged within said first bolt holder threaded bore.

8. A test fixture as defined in claim 7 in which said strain module comprises a second bolt holder pivotally connected to said second lever arm, and where said load bolt comprises a second threaded end opposite said first threaded end, said second bolt holder including a threaded bore for receiving said second threaded end of said load bolt in threaded engagement, said second threaded end and said second bolt holder threaded bore threaded in an opposite helical direction from said first threaded end and from said threaded bore of said first bolt holder.

9. A test fixture as defined in claim 7 in which said stress module comprises:

a spring having inner and outer opposite ends;
an inner spring retainer abutting said spring inner end and including a threaded aperture to receive said second threaded end of said load bolt in threaded engagement; and
an outer spring retainer abutting said spring outer end and including a releasable lever arm connector for releasably connecting to one of said lever arms.

10. A test fixture as defined in claim 9 in which said lever arm connector of said outer spring retainer is a fixed non-pivotal connector.

11. A tensile test fixture for applying constant tensile forces to a tensile specimen, said test fixture comprising:

first and second mounting grips for holding opposite ends of a tensile test specimen;

a frame supporting said first and second mounting grips for relative reciprocal movement toward and away from one another;

said frame comprising a pivoted lever arm structure including first and second lever arms connected to a compression column at first and second compression column connecting points and extending transversely to respective first and second force-application points, at least one of said lever arms being pivotally connected to said compression column, said first and second mounting grips supported on said first and second lever arms, respectively, said first mounting grip disposed between said first compression connecting point and said first force-application point and said second mounting grip disposed between said second compression connecting point and said second force-application point, and a force-applying assembly including first and second opposite ends connected to said first and second lever arm force-application points, respectively; and said force-applying apparatus including interchangeable strain and stress modules.

12. A test fixture as defined in claim 11 in which both said lever arms are pivotally connected to said compression column.

13. A test fixture as defined in claim 11 in which said force-applying assembly comprises:

a first bolt holder including an outer end pivotally connected to said first lever arm, said first bolt holder including a threaded bore disposed in an inner end of said first bolt holder opposite said outer end; and a load bolt having a first threaded end threadedly and adjustably engaged within said first bolt holder threaded bore.

14. A test fixture as defined in claim 13 in which said strain module comprises a second bolt holder pivotally connected to said second lever arm, and where said load bolt comprises a second threaded end opposite said first threaded end, said second bolt holder including a threaded bore for receiving said second threaded end of said load bolt in threaded engagement, said second threaded end and said second bolt holder threaded bore threaded in an opposite helical direction from said first threaded end and from said threaded bore of said first bolt holder.

15. A test fixture as defined in claim 13 in which said stress module comprises:

a spring having inner and outer ends;

an inner spring retainer abutting said spring inner end and including a threaded aperture to receive said second threaded end of said load bolt in threaded engagement; and an outer spring retainer abutting said spring outer end and including a releasable lever arm connector.

16. A test fixture as defined in claim 15 in which said lever arm connector of said outer spring retainer is a non-pivotal connector.

\* \* \* \* \*